United States Patent [19]

Round

[11] 4,353,260
[45] Oct. 12, 1982

[54] SHIELD FOR GAS SAMPLING PROBE

[75] Inventor: Robert T. Round, Riverton, Wyo.

[73] Assignee: Texasgulf Inc., Stamford, Conn.

[21] Appl. No.: 192,352

[22] Filed: Sep. 30, 1980

[51] Int. Cl.$^3$ .............................................. G01N 1/20
[52] U.S. Cl. .............................. 73/863.41; 73/863.61;
73/863.21; 204/195 S
[58] Field of Search ........... 73/863.11, 863.21, 863.51,
73/863.58, 863.71, 349, 863.61; 204/195 S

[56] References Cited

U.S. PATENT DOCUMENTS

| 3,765,226 | 10/1973 | Strickland | 73/863.61 |
| 4,064,756 | 12/1977 | MacLean | 73/349 |
| 4,184,934 | 1/1980 | Bode et al. | 204/195 S |
| 4,215,565 | 8/1980 | Zanker | 73/863.61 |

Primary Examiner—S. Clement Swisher
Attorney, Agent, or Firm—Denis A. Polyn

[57] ABSTRACT

A shield for a gas sampling probe is disclosed. The shield includes a tubular member which substantially encloses the probe. Openings are provided in the tubular member to permit a gas flow into the shield past the probe.

21 Claims, 2 Drawing Figures

SHIELD FOR GAS SAMPLING PROBE

BACKGROUND OF THE INVENTION

The present invention relates generally to a shield for a sampling or monitoring unit or probe which is inserted into a gas flow to measure, monitor or sample one or more gases. More particularly, the present invention relates to a shield for a probe of an oxygen, sulfur dioxide and nitrous oxide monitoring or sampling unit, the respective probe being surrounded by a porous filter and extending into a gas flow typically within a stack, transition piece or other gas conduit or the like to monitor or sample the oxygen, sulfur dioxide and nitrous oxide contents of the gases passing therethrough.

Combustion or process gases are monitored for environmental purposes to determine emissions prior to release to the atmosphere, to determine combustion efficiency, and for other purposes. Probes used to sample such gases are typically inserted into a stack or other gas conduit such as a transition piece, and must operate under varied conditions of heat and exposure to gases, water, steam and particulate matter.

For example, in sampling the combustion products of coal, a probe can be exposed to temperatures typically in the range of about 60° F. to about 200° F. and higher, and can be exposed to gases such as sulfur dioxide, nitrous oxide, carbon dioxide and carbon monoxide, to steam and water, and to particulate matter such as soot and ash. The particulate matter which may reach the probe is typically extremely fine, having escaped removal by scrubbing systems and electrostatic precipitators located upstream (relative to the gas flow) of the probe. A ceramic or other porous filter is provided to enclose the probe, thereby filtering any particulate matter which has reached the filter and preventing such particulate matter from reaching the probe itself, while permitting the gases to pass through the filter and reach the probe. The amount of water that the filter is exposed to can be considerable, particularly on cool days when the stack or conduit carrying the gases is at the dew point, thereby causing condensation of water vapor in the stack or conduit. During the use of such a probe, there is a tendency for water to accumulate on the exterior surface of the filter. The water causes the particulate matter which, as mentioned, is extremely fine, to become moistened and to adhere to and cake or become encrusted on the filter. In a very short time, the filter becomes entirely clogged or "blinded" by the encrusted particulate matter.

In one prior art oxygen probe having a ceramic filter, the ceramic filter was exposed directly to the gases, water and particulate matter except for a portion of the ceramic filter which faced upstream of the gas flow. That portion was shielded by a V-shaped member. The apex of the V faced upstream of the gas flow and acted to blunt the flow of gases and particulate matter around the ceramic filter. However, a substantial portion of the ceramic filter was directly exposed, and water and particulate material tended to accumulate on the filter, as mentioned above. As a result, the particulate matter became moistened and caked on the ceramic filter. In a short time, not unusually after only a few days of use, the ceramic filter become encrusted and clogged.

OBJECTS AND SUMMARY OF THE INVENTION

It is an object of the present invention to prolong the life of a probe which monitors or samples gases, particularly a probe whose active portion is enclosed by a porous filter.

It is another object of the invention to prevent the clogging of a filter, particularly a porous filter, for a probe used to monitor or sample gases.

It is still another object of the present invention to prevent particulate matter from combustion, particularly of coal, from reaching a probe and/or from reaching a filter enclosing the active portion of the probe, the probe being disposed in a gas flow typically in a stack, transition piece or other conduit for sampling combustion gases.

It is another object of the invention to prevent the accumulation of moisture on such a probe and/or filter.

In accordance with the invention, the probe and/or a porous filter enclosing the probe are covered by a shield so that the probe and/or filter are substantially not directly exposed to the particulate matter and water in a gas flow, and water and moisture are substantially prevented from accumulating on the probe and/or filter. Means are provided in the shield to define a passage communicating the interior of the shield with the exterior thereof for permitting a flow of gases from the exterior of the shield to the interior of the shield and then to the exterior of the shield again.

The passage means is structured to provide a pressure head to the gas flow impinging on the shield and at the same time creates a partial vacuum which assists in drawing gases into the passage means. The pressure head is effective to reduce the quantity of gases which are otherwise allowed to enter into the shield. The probe, as a result, samples only a minor part of the gases passing by the shield. Yet, the gas entering the shield is sufficient to provide a good statistical representative of the entire gas flow.

The passage means comprise openings in the shield which define an entrance into and an exit from the shield. The area of the entrance and exit openings is unequal and affects the magnitude of the pressure head produced. Preferably, the area of the entrance opening or openings is at least about 1.25 times greater than the area of the exit opening or openings. The area of the openings is substantially smaller than the surface area of the shield surrounding the active portion of the probe.

In a disclosed embodiment, the probe is utilized with a porous filter which allows gases to reach the probe but prevents particulate matter from reaching the probe. In accordance with the invention, the porous filter is covered by the shield so that the filter itself is not substantially directly exposed to the particulate matter. Rather, openings provided in the shield permit the gases to reach the filter while the shield substantially prevents the particulate matter from reaching the filter. The shield also deters the accumulation of water and moisture thereon as well as substantially preventing water and moisture from reaching the interior thereof and the filter. Since water and moisture are substantially not permitted to enter into the shield and reach the filter, any particulate matter which may enter into the shield does not become moistened and therefore does not cake on the filter. Rather, the particulate matter may form on the exterior shield surface as a thin, dry layer of fine powder which can easily be removed. Any particulate matter which enters and remains in the interior of the shield is essentially not moistened and is also in the form of a fine dry powder which can easily be removed.

Certain probes operate at high temperatures in sampling gases. For example, one oxygen probe comprising zirconium oxide and available from Westinghouse Corp. operates at a temperature of about 1500° F. Quite surprisingly, the applicant has found that a shield which substantially surrounds a probe operating at such a relatively high temperature acts to drive off any water and moisture which may enter into the shield and thereby assists in preventing accumulation of water and moisture within the shield. The probe also heats the shield and similarly assists in preventing accumulation of water on and moistening of the shield exterior surface. As a result, shielding performance is enhanced. Although not wishing to be bound by any theory, the applicant believes that the shield enclosing the probe creates an oven effect which cooperates with a reduced gas flow in the shield to drive off any water and moisture entering into the shield and to prevent accumulation of any water and moisture impinging on the exterior of the shield.

More specifically, in accordance with the invention, a shield is provided for a probe adapted to sample gases typically in a stack, transition piece or other conduit. The shield according to the invention comprises an elongated member adapted to receive and substantially enclose the probe, and means in the elongated member defining a passage communicating the interior of the elongated member with the exterior thereof for permitting a flow of gases from the exterior of the elongated member to the interior thereof and then to the exterior thereof again. Means are also provided in accordance with the invention for mounting the elongated member to extend transversely in the gas flow, i.e. the gas flow of the stack or simply, the main gas flow.

The passage means preferably produces a pressure head to the flow of gases therethrough which is operative to restrict the gas flow into the shield to be a minor part, preferably a small fraction, of the entire gas flow past the shield. In a disclosed embodiment, the passage means comprises a plurality of openings in the elongated member, the relative areas of the openings affecting the magnitude of the pressure head. The openings are preferably disposed so that the gases enter the openings at an angle, or transversely to the main flow of the gases.

In an embodiment of the invention, the passage means comprises at least one transverse opening forming a passage through the elongated member transversely of the elongation of the elongated member and at least one axial opening through the elongated member generally axially thereof. The axial opening is preferably located in the elongated member to face in the downstream direction of the main gas flow. Thus, neither the transverse or axial opening faces or opens directly upstream of the main gas flow, i.e., neither opens opposite and parallel to the main gas flow. As a result, gas can only enter the shield by passing transversely (at an angle) through the transverse opening. The axial opening is defined by opposed ends and an extent therebetween, the area of the axial opening being substantially less than the surface area of the elongated member for a longitudinal distance corresponding to the extent of the axial opening. Preferably, the transverse opening has an area which is at least about three-fourths of the cross-sectional area of the elongated member and the area of the transverse opening is at least about 1.25 times larger than area of the axial opening and preferably in the range of about 1.5 to 2 times larger than the area of the axial opening. It is preferred that the axial opening be elongated and extend generally axially along the elongated member. The axial opening is preferably an axial slot.

In another embodiment, the axial opening faces upstream and means are disposed substantially coextensive with and spaced from the axial opening to prevent gases from entering the axial opening white permitting gases to exit from the axial opening.

In the disclosed embodiment, the elongated member is tubular having a generally open end adapted to extend within the gas flow and an axial slot in the tubular member adjacent the open end. The axial slot has a width which is substantially less than the circumference of the tubular member. Additionally, the open end of the tubular member may include means therein for stiffening or supporting the tubular member against compressive forces.

These and other aspects of the present invention will be more apparent from the following description of the preferred embodiment of the invention taken in conjunction with the accompanying drawings and appended claims.

BRIEF DESCRIPTION OF THE DRAWINGS

The present invention is illustrated by way of example and not limitation in the figures of the accompanying drawings in which like references indicate similar parts and in which.

DESCRIPTION OF THE PREFERRED EMBODIMENT

Figure 1:
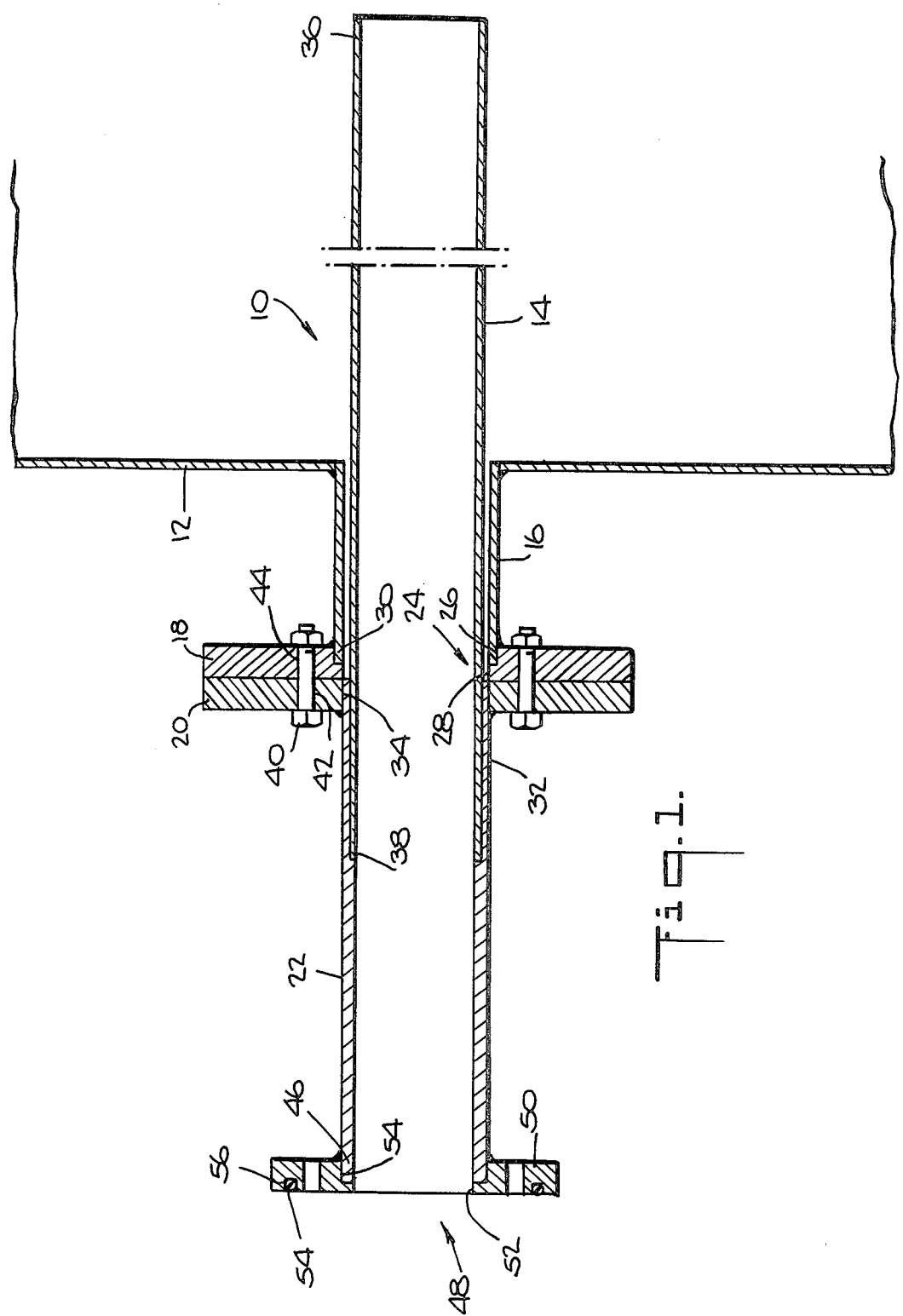
FIG. 1 is a side view of the shield according to the invention mounted in a stack.

Referring now more particularly to the drawings, the shield 10 according to the invention is illustrated in FIG. 1 mounted in a stack 12 for sampling flue gases produced from the combustion of coal. In particular, the probe detects the presence of oxygen in the flue gases and is connected to a remotely located unit which determines the quantity of oxygen in the flue gases. It is to be understood, however, that the invention is not limited to shielding a probe which samples flue gases from the combustion of coal, or to shielding an oxygen probe, but is applicable to shielding a probe for sampling and detecting other gases in other environments. For example, the invention is applicable to shielding a sulfur dioxide or nitrous oxide probe. The shield 10 is mounted in a stack 12 illustrated to be made of metal which is glass-lined. However, the shield 10 may also be mounted in stacks made of other material, for example, masonry or refractory material which are glass-lined or otherwise treated to resist corrosion by the gases and reactants thereof.

Figure 2:
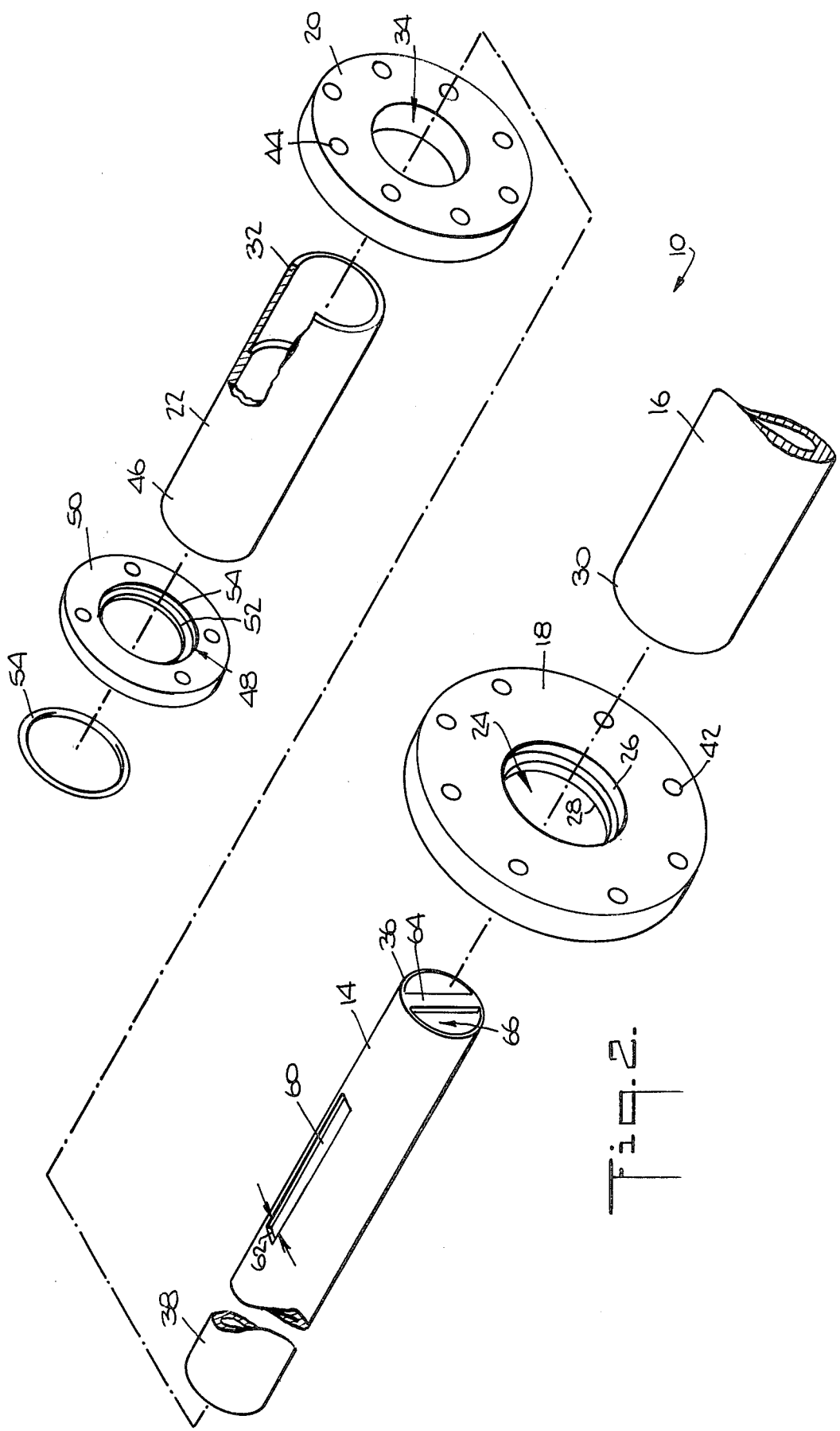
FIG. 2 is an exploded prospective view of the shield of FIG. 1.

Referring now to both FIGS. 1 and 2, the shield 10 comprises a shield member 14 which extends generally to about the center of the gas flow in the interior of the stack 12. The shield member 14 extends generally horizontally into the vertical flow of the flue gases. By way of example, the shield member can be about 75 inches long and three inches in diameter for a 14 feet diameter stack.

The shield member 14 can be mounted in the stack 12 by means of a sleeve 16, flanges 18 and 20, and an adapter sleeve 22. The shield member 14, the sleeve 16 and the adaptor sleeve 22 are preferably tubular as shown, and the flanges are annular having central openings therethrough also as shown. Typically, the sleeve 16 is metal and is secured to a metal stack by welding. Briefly, the sleeve 16 is secured to the stack, the flange 18 is secured to the sleeve 16, the flange 20 is secured to the flange 18, the shield member 14 is secured to the adaptor sleeve 22 and the adaptor sleeve 22 is secured to the flange 20.

The flange 18 has a central circular opening 24 which includes a larger diameter portion 26 and a smaller diameter portion 28. The larger diameter portion 26 is adapted to receive the end 30 of the sleeve 16 with the smaller diameter portion 28 acting as a shoulder against which the end 30 of the sleeve 16 abuts. The sleeve end 30 is preferably welded in the central opening 24 of the flange 18. The flange 18 and sleeve 16 remain secured to the stack while removal and insertion of the shield member 14 may be accomplished wholly from the exterior of the stack.

One end 32 of the adaptor sleeve 22 extends through the central opening 34 of flange 20 and is welded therein, the diameter of the opening 34 being sized to receive end 32 of the adaptor sleeve. The shield member 14 includes opposed ends 36 and 38, the end 36 extending within the stack and the end 38 projecting to the exterior of the stack. The end 38 of the shield member 14 extends into the adaptor sleeve 22 welded in the central opening 34 of the flange 20. The end 38 of the shield member is received in the end 32 of the adapter sleeve 22 which is of a reduced diameter, and is welded therein. Thus, the flange 20, the adaptor sleeve 22 and the shield member 14 are secured together. This assembly is secured to flange 18 by bolting the flanges 20 and 18 together by means of a plurality of bolts 40 extending through circumferentially disposed holes 42, 44 in the flanges.

The end 46 of the adaptor sleeve 22 is received in the central opening 48 of another flange 50 and is welded therein. The central opening 48 in the flange 50 also includes a smaller diameter portion 52 and a larger diameter portion 54. The larger diameter portion receives the end 46 of adaptor sleeve 22 with the larger diameter portion forming a shoulder against which the end 46 abuts. The end 46 is then welded in the opening 48. An O-ring 54 is inserted in an annular groove 56 in the exterior face of the flange 50 so that a fluid-tight seal can be obtained between a coupling assembly (not shown) and the flange. Electrical conductors (not shown) extend from the probe through the coupling assembly to monitoring equipment remotely located from the probe.

With the arrangement illustrated in FIGS. 1 and 2 as described above, it is possible to remove the shield member 14 by disconnecting the flange 20 from the flange 18 and withdrawing the assembly comprising the shield member 14, the flange 20, the adaptor sleeve 22, the flange 50 and the coupling assembly. If it is desired only to remove the probe member, then it is only necessary to decouple the coupling assembly from flange 50 and remove the probe.

The shield member 14 includes an axial slot 60 (FIG. 2) disposed adjacent to the end 36 of the shield member. The width 62 of the slot 60 is substantially less than the outer perimeter (circumference) of the shield member 14. The end 36 of the shield member 14 is open except for a member 64 which extends in the open end of the shield member, the spaces between member 64 and the inner surface of the shield member defining transverse opening 66. Member 64 is optional and its purpose is to provide support for the shield and to stiffen it. The transverse opening 66 provides an entrance for the gases into the interior of the shield member and the slot 60 provides an exit for gases from the shield member. The slot is located in the top (relative to FIG. 2) of the shield member and is therefore downstream of the main gas flow relative to the shield and does not open or face upstream of the main gas flow. As a result, gases do not enter the slot 60. Since the axis of the shield is approximately horizontal, the transverse opening is approximately at a right angle to the flow of the flue gases. Therefore, the transverse opening also does not open or face upstream of the main gas flow.

The area of the member 64 is substantially less than the cross-sectional area of the shield member such that the resulting opening 66 has an area which is at least about three-fourths of the cross-sectional area of the shield member.

The area of the transverse opening 66 at the end 36 of the shield member 16 is approximately 1.5 to 2 times the area of the slot 60. For the three inch diameter shield member mentioned above, the slot is about five inches long and one-half inch wide. The difference in areas between slot 60 and opening 66 in cooperation with the flow of gas past the transverse opening creates a pressure head to the flue gases entering the shield and thereby reduces the quantity of gas entering opening 66 into the shield. The gases moving past the transverse opening 66 create a partial vacuum in the shield which assists in drawing the gases into the shield through the transverse opening. The gas pressure in a stack carrying the combustion products of coal can be about one-half inch to about one inch of water.

In the embodiment illustrated, although the invention is not so limited, the shield is advantageously used for an oxygen probe which is surrounded by a ceramic filter. The probe with the ceramic filter (not shown) are axially disposed within the shield member 14. As a result, the ceramic filter and probe are essentially not directly exposed to the flue gases in the stack. The flue gases enter into the interior of shield member 14 through the transverse opening 66, which opens at an angle to the flow of the flue gases, and exit from slot 60 which is downstream of the gas flow relative to the shield.

The particulate matter substantially does not reach the interior of shield member 14. Thus, the particulate matter is prevented from reaching the ceramic filter. Also, since water is essentially prevented from entering into the shield member 14 and is prevented from accumulating on the exterior thereof, any particulate matter reaching the shield member or the filter does not become moistened and therefore will not cake on the shield member or filter, but may form as a fine, dry powder which can easily be removed.

As oxygen probe of the zirconium oxide type used in the arrangement described above creates in accordance with the applicant's belief an oven effect, as described above. The probe is at about 1500° F. during sampling and the heat generated within the shield member acts to drive off moisture which may have passed into the interior of the shield and thereby assists in preventing accumulation of moisture on the ceramic filter, as well as on the shield member itself. This essentially prevents encrusting of any particulate matter which may enter into the interior of the shield member or accumulate on the exterior surface of the shield member.

The applicant has found that a zirconium oxide probe when utilized with a shield according to the invention, enables use of the ceramic filter and probe for extended periods of time. Where the prior art probe and shield arrangement described above had to be changed as often as every other day, a shield according to the invention allowed use of a zirconium oxide probe with a ceramic filter for six weeks, at which time the ceramic filter was essentially free of encrusted particulate matter. Although not wishing to be bound by any theory, the applicant believes that the superior performance of the shield when used with such a probe, which was surprising and unexpected, is due in part to the oven effect created within the shield.

The shield according to the invention may also be used with a "cold" probe, for monitoring sulfur dioxide for example. A cold probe operates at approximately the temperature of its environment. Such a shield includes a shield member 14 disposed in the gas flow such that the slot 60 opens into the gas flow. A V-shaped member is disposed adjacent to and spaced from the slot directly in the gas flow, with the apex of the V facing upstream. The V-shaped member is substantially coextensive with the slot and forces the gases to flow around the slot and prevents the gases from flowing into the slot. This arrangement also produces turbulence which assists the gases to enter the transverse opening.

A shield fabricated in accordance with the invention is made of a material which resists corrosion in its intended environment of use. For example, when used to shield a "hot" zirconium oxide probe, the shield is preferably made of Hastoly-X and when used to shield a "cold" nitorus oxide probe, the shield is preferably made of Teflon. Additionally, the shield is dimensioned to receive the particular probe (and filter) it is intended to shield.

The advantages of the present invention as well as certain changes and modifications of the disclosed embodiment thereof, will be readily apparent to those skilled in the art. It is the applicant's intention to cover by his claims all those changes and modifications which could be made to the embodiment of the invention herein chosen for the purpose of the disclosure without departing from the spirit and scope of the invention.

What is claimed is:

1. A shield for a probe adapted to sample gases comprising an elongated member adapted to receive and substantially enclose the probe, said elongated member having an end facing generally in the direction of elongation of the elongated member, means associated at least in part with the end of the elongated member disposed facing the exterior of the elongated member generally in the direction of elongation of the elongated member for permitting a gas to flow from the exterior of the elongated member to the interior of the elongated member and again to the exterior of the elongated member, the elongated member being adapted to be disposed in use so that gas enters the elongated member through said means transversely of the main gas flow exteriorly of the shield.

2. The shield according to claim 1 and including means for mounting the elongated member to extend transversely of said main gas flow.

3. The shield according to claim 1, wherein said means is operative to provide a pressure head to gas entering the elongated member.

4. The shield according to claim 1, wherein said means comprises a plurality of openings in the elongated member.

5. The shield according to claim 1, wherein said means comprises at least one opening for admitting gas into the elongated member and at least one opening for permitting gas to exit from the elongated member.

6. The shield according to claim 5, wherein the opening for admitting gas is at least about 1.25 times larger than the opening for permitting gas to exit.

7. The shield according to claim 1, wherein said means comprises a first opening in said end forming an entrance passage for gas to enter into the elongated member transversely of the direction of elongation of the elongated member and a second opening in the elongated member having an extent extending generally in the direction of elongation of the elongated member.

8. The shield according to claim 7, wherein the area of the second opening is substantially less than the surface area of the elongated member for a longitudinal distance corresponding to said extent of the second opening.

9. The shield according to claim 7, wherein the area of the first opening is at least about 1.25 times larger than the area of the second opening.

10. The shield according to claim 7, wherein the second opening is elongated.

11. The shield according to claim 7, wherein the second opening extends generally axially along the elongated member.

12. The shield according to claim 1, wherein the elongated member is tubular and includes an axial slot therealong, the axial slot having a width which is substantially less than the circumference of the tubular member, the tubular member being generally open at said end for permitting said gas flow from the exterior of the elongated member to the interior thereof, the axial slot being located adjacent to said end and permitting said gas flow from the interior to the exterior of the elongated member, said slot and said generally open end comprising said means.

13. The shield according to claim 2, wherein the means for mounting are adapted to mount the elongated member in a conduit in which the gases are flowing generally parallel to the axis of the conduit, the means for mounting comprising a sleeve adapted to be secured to the conduit with the axis of the sleeve being transverse to the axis of the conduit, a first member secured to the sleeve, a second member secured to the elongated member, and means for securing the first and second members together such that the sleeve and the elongated member are coaxially disposed.

14. The shield according to claim 13, wherein the first and second members are flanges having openings therein in which the sleeve and elongated member are respectively secured.

15. A shield for a probe adapted to sample gases in a conduit comprising:
a tubular member adapted to receive and enclose the probe,
a first opening in an end of the tubular member adapted to extend in the conduit, said first opening facing generally in the axial direction of the tubular member;

a second opening extending along the surface of the tubular member adjacent to said end, said openings defining a passage communicating the interior of the tubular member with the exterior thereof for permitting a flow of gases from the exterior of the tubular member to the interior and then to the exterior again; and means for mounting the elongated member to extend transversely in the conduit.

16. The shield according to claim 15, wherein the area of the first opening is at least about 1.25 times larger than the area of the second opening.

17. The shield according to claim 16, wherein the second opening is defined by opposed ends and an extent therebetween, the area of the second opening being substantially less than the surface area of the tubular member for a longitudinal distance corresponding to the extent of the second opening.

18. The shield according to claim 15, wherein the means for mounting comprises a tubular sleeve adapted to be secured to the conduit with the axis of the sleeve being transverse to the axis of the conduit, a first member secured to the sleeve, a second member secured to the tubular member, and means for securing the first and second members together such that the sleeve and the tubular member are coaxially disposed.

19. The shield according to claim 18, wherein the first and second members are flanges having openings therein in which the sleeve and tubular member are respectively secured.

20. The shield according to claim 14, wherein the means for mounting includes a further sleeve having an opening into which the elongated member extends and is secured, the further sleeve extending into the opening of the second flange and being secured thereto.

21. The shield according to claim 19, wherein the means for mounting includes a further sleeve having an opening into which the elongated member extends and is secured, the further sleeve extending into the opening of the second flange and being secured thereto.

* * * * *